United States Patent [19]

Hange et al.

[11] Patent Number: 5,344,950

[45] Date of Patent: * Sep. 6, 1994

[54] PROCESS FOR THE PREPARATION OF VINYLCHLOROSILANES

[75] Inventors: Willy Hange, Wittlingen; Helmut Dietsche; Claus-Dietrich Seiler, both of Rheinfelden, all of Fed. Rep. of Germany

[73] Assignee: Hüls Aktiengesellschaft, Marl, Fed. Rep. of Germany

[*] Notice: The portion of the term of this patent subsequent to Dec. 24, 2008 has been disclaimed.

[21] Appl. No.: 7,415

[22] Filed: Jan. 25, 1993

Related U.S. Application Data

[62] Division of Ser. No. 642,250, Jan. 4, 1991, abandoned.

[30] Foreign Application Priority Data

Jan. 23, 1990 [DE]  Fed. Rep. of Germany ....... 4001820

[51] Int. Cl.$^5$ ................................................ C07F 7/14
[52] U.S. Cl. ..................................... 556/478; 556/481
[58] Field of Search ................................. 556/478, 481

[56] References Cited

U.S. PATENT DOCUMENTS 5,075,480  12/1991  Hange et al. ..................... 556/481

Primary Examiner—Joseph L. Schofer
Assistant Examiner—Tom Weber
Attorney, Agent, or Firm—Felfe & Lynch

[57] ABSTRACT

A process for the continuous production of vinylchlorosilanes by reacting vinyl chloride with chlorosilanes at elevated temperature consists of a heatable reaction tube having an internal diameter $d_1$ and a tubular displacement body having an external diameter $d_2$ mounted within the reaction tube in an axially symmetrical arrangement and extending over the entire length of the reaction tube, the diameter $d_2$ being smaller than the diameter $d_1$.

1 Claim, 1 Drawing Sheet

PROCESS FOR THE PREPARATION OF VINYLCHLOROSILANES

This is a Divisional Application of application Ser. No. 07/642,250, filed Jan. 4, 1991, now abandoned.

FIELD OF THE INVENTION

The present invention relates to a novel reactor for the continuous preparation of vinylchlorosilanes, especially of vinyltrichlorosilane, by reacting vinyl chloride with chlorosilanes.

BACKGROUND OF THE INVENTION

Vinylchlorosilanes, in particular vinyltrichlorosilane, are useful products which are widely used in industry. For instance, they are used for sizing of glass fabrics and in the production of vinylpolysiloxanes.

German Patent No. 936,445, German Offenlegungsschrift No. 22 10 189 and particularly German Patent No. 20 02 258 disclose that when mixtures of vinyl chloride and chlorosilanes and in particular mixtures of vinyl chloride and trichlorosilane are passed through appropriately heated tubes made of ceramics, glass or iron, industrially acceptable yields of vinylchlorosilanes or vinyltrichlorosilane are obtained. In the case of vinyltrichlorosilane, yields of about 50 to 98% are reached, depending on the ratio of the starting components to one another, based on the conversion of the component which is used in less than a stoichiometric amount. These results are achieved when reaction tubes having an internal diameter of 2.5 to 3.5 cm and a length of 122 to 150 cm, mean residence times of the reactants of 0.2 to 20 seconds, reaction temperatures of 400° to 750° C. and pressures of 1 to 3 bar are used. Depending upon the choice of dimensions of the reactor tube and on the reaction parameters, 0.8 to 3.2 tons per month of vinyltrichlorosilane can be produced in such reactors.

The sudden increase in the demand for vinylchlorosilanes, especially for vinyltrichlorosilane, made it necessary to try to increase the output per reaction unit.

According to German Patent No. 20 02 258, particularly good yields are obtained if the internal diameter of the reactor is about 35 mm. In an attempt to increase the output of the unit by enlarging the internal diameter of the reactor, and thus to increase the throughput per unit time, it has been determined that, although a limited increase in the output of the reactor unit occurs up to an enlargement of the internal diameter to 50 mm, this is far from proportional to the increase in the cross-sectional area of the reactor tube. With a further enlargement of the internal diameter of the reactor tube, even a decrease in the achievable output of vinyltrichlorosilane relative to the cross-sectional area of the reactor occurs. Consequently, it is impossible to increase the space-time yield of vinylchlorosilanes in the known tube reactors by enlarging the internal diameter of the reactor tube.

OBJECTS OF THE INVENTION

Since it is possible only within limits to increase the space-time yield of a tube reactor by shortening the residence time of the reaction gases in the reactor, it is an object of the present invention to provide a novel reactor type for the reaction of chlorosilanes with vinyl chloride which makes it possible to control the vinylchlorosilane output in such a way that it increases as proportionally as possible to the enlargement of the reaction area, that is, to the cross-sectional area of the reactor. At the same time the reaction area should be capable of unlimited enlargement and make it possible to obtain vinylchlorosilane yields of between 20 and 70 tons per month, preferably between 30 and 50 tons per month.

Other objects and advantages of the invention will become apparent as the description thereof proceeds.

BRIEF DESCRIPTION OF THE DRAWING

The attached drawing is a schematic representation of the reactor according to the present invention, in which.

DESCRIPTION OF THE INVENTION

Figure 1:
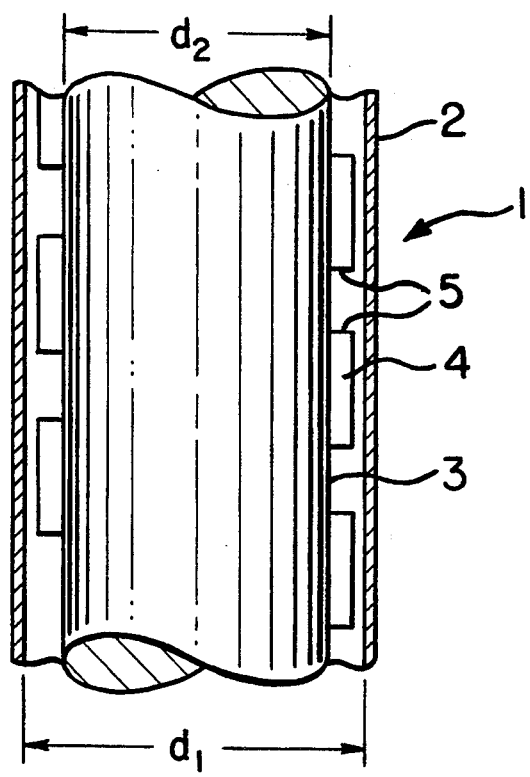
FIG. 1 is a side view in partial section of the reactor.
Figure 2:
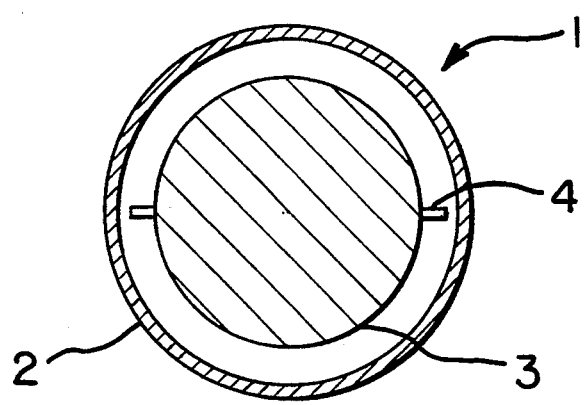
FIG. 2 is an end view of the reactor in partial section.

Referring now to the drawing, we have discovered that the above objects are achieved by using for the reaction of vinyl chloride and chlorosilanes to yield vinylchlorosilanes a reactor which is made of a ferrous construction material and consists of a heatable tube 2 having an internal diameter $d_1$, and having mounted in its interior in axially symmetric arrangement a cylindrical displacement body 3 which extends over the entire length of the tube 2, the displacement body 3 having an external diameter $d_2$, $d_2$ being smaller than $d_1$, whereby an annular gap G is formed. The displacement body is preferably formed as a tube closed at both ends or as a solid roll.

In this form of reactor design any desired size of cross-sectional area $R_f$ of the annular gap G [$R_f = (d_1^2 - d_2^2) \times \pi/4$] can be obtained, depending on the internal diameter $d_1$ of the outer tube 2 and on the external diameter $d_2$ of the displacement body 3. We have further discovered that the reaction of vinyl chloride and chlorosilanes to yield vinylchlorosilanes takes place in such a reactor unit in the direction of the stated object of the invention only if the following relationship applies between the internal diameter $d_1$ of the outer tube and the external diameter $d_2$ of the displacement body:

$$d_1 = d_2 + G,$$

where G is less than or equal to 5 cm. Even if the dimensions of the reactor deviate only slightly from the condition $$d_1 = d_2 + G,$$

where G is less than or equal to 5 cm, we have found that in reactor units designed according to the present invention, the output of vinylchlorosilane no longer increases proportionally to the increase in the cross-sectional area of the annular reactor gap and may even cause the reaction to stop.

Of course, the gap G must have a minimum value which depends upon the diameters $d_1$ and $d_2$ and is generally about 1 cm. Reactor units in which G is equal to 4 cm have proved particularly suitable for industrial use.

The length L of the reactor is adapted to the specific requirements of the particular reaction of vinyl chloride with chlorosilanes. For example, in the case of the reaction of vinyl chloride with trichlorosilane to yield vinyltrichlorosilane in the temperature range of around 650°

C. and with residence times of less than 2 seconds, reactors 200 to 280 cm in length have proved to be suitable. A significant reduction in the length of the reactor leads to a less complete conversion; an increase in the reactor length causes a drop in the conversion to occur in this temperature range.

The heating of the reactor, that is, of the outer tube 2, can be effected in the most diverse ways. The means most frequently used consists of direct electrical heating of the outer surface of the tube. In another type of heating, the outer tube is heated by means of an interposed medium, for example molten lead. The outer tube may also be heated with a gas flame. The manner of heating only in significantly affects the conversion achievable per cross-sectional area of the annular reactor gap.

The displacement body 3 which is axially symmetrically mounted in the interior of the outer tube 2 has the shape of a cylinder. Its surface is at a perpendicular distance G/2 from the inner surface of the outer tube 2. The displacement body is made of the same or similar material as the outer tube. The distance from the outer surface of the displacement body to the inner surface of the outer tube can be very small.

In general, the displacement body 3 has the same length as the outer tube 2. If the displacement body is substantially shorter than the outer tube, this leads to yield reductions.

During the operation of the reactor, the displacement body 3 can be at rest or, alternatively, may be rotated about its longitudinal axis. We have found that the results obtained with the displacement body at rest are less satisfactory than if it is rotated. The rotary motion of the displacement body has a positive effect on the achievement of optimum results; it is sufficient if the rate of revolution is maintained within the range of 5 to 100 r.p.m. The preferred rate of revolution of the displacement body is 40 to 60 r.p.m. An increase of the rate of revolution to more than 100 r.p.m. is of no advantage.

For the purpose of stabilizing the rotary motion of the displacement body 3 and improving the mixing of the reactants in the reaction space G between the inner wall of the outer tube 2 and the outer wall of the displacement body 3, it has proved to be advantageous to attach metal strips 4 to the outer surface of the displacement body 3 which protrude into the reaction space perpendicular to the surface of the displacement body. These strips preferably extend essentially parallel to the axis of the displacement body. However, they can also be arranged at an acute angle to the axis of the displacement body. They can also take the shape of a continuous strip over the entire length of the displacement body, but they can also be attached as offset pieces distributed over the surface of the displacement body. It has proved to be expedient if the radial edge 5 of the metal strips attached to the surface of the displacement body is 1 to 2 mm shorter than G/2.

The materials of which both the outer tube and the displacement body are made include ferrous alloys such as, for example, scale-free steel which contains chromium, nickel and/or titanium and/or molybdenum as alloy constituents in addition to iron.

The reactor of the present invention for the production of vinylchlorosilanes by reaction of vinyl chloride with chlorosilanes can be arranged either horizontally or vertically, or also at an inclination. The manner of arranging the reactor has no effect on the vinylchlorosilane output of the reaction unit. However, we have found that the durability of a vertically arranged reactor is substantially greater than that of a reactor which is operated in a horizontal position.

For the reaction of vinyl chloride with chlorosilanes in the reactor according to the present invention, with adjustment of the reaction conditions in accordance with the specific requirements of the chlorosilane which is employed, the chlorosilane compounds which are used may be, for example, methylhydrogendichlorosilane, ethylhydrogendichlorosilane or trichlorosilane.

The following Examples illustrate the present invention and will enable others skilled in the art to understand it more completely. It should be understood, however, that the invention is not limited solely to the particular Examples given below.

EXAMPLES 1 TO 5

Vinyl chloride and trichlorosilane were premixed in a 1:1.4 molar ratio, and the mixture was introduced into the individual reactors shown in the Table below. All of the reactor parts were made of an alloyed steel of type 1.4828. The reaction temperature was about 660° C., and the residence time was about 1.8 seconds. The rate of revolution of the displacement body was 50 r.p.m. in all cases. The reaction mixture leaving the reactor was condensed and worked up in a distillation column. The monthly output of the individual reactors (tons per month) is also shown in the Table below.

Example 5 is a comparison Example: It shows that the output decreases considerably when the value of G is increased. The output is only about 5 tons per month/100 cm² of cross-sectional area of the annular gap G, whereas according to the present invention the output is more than 12 tons per month/100 cm² of cross-sectional area of the annular gap G.

TABLE

| Example | Reactor dimensions (cm) | Cross-sectional area Rf of annular gap G (cm²) | Vinyltrichlorosilane outputs (tons per month) |
|---|---|---|---|
| 1 | $d_1 = 60$<br>$d_2 = 56$<br>$G = 4$<br>$L = 250$ | 364 | 47 |
| 2 | $d_1 = 30$<br>$d_2 = 26$<br>$G = 4$<br>$L = 230$ | 176 | 25 |
| 3 | $d_1 = 50$<br>$d_2 = 46$<br>$G = 4$<br>$L = 250$ | 302 | 39 |
| 4 | $d_1 = 50$<br>$d_2 = 48$<br>$G = 2$<br>$L = 250$ | 154 | 20 |
| 5 (Comparison Example) | $d_1 = 50$<br>$d_2 = 43$<br>$G = 7$<br>$L = 250$ | 511 | 26 |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. In a process for the continuous reaction of vinyl chloride with a chlorosilane to produce a vinylchlorosilane, the improvement which comprises performing the reaction in a vertically arranged reactor comprising a heatable reaction tube having an internal diameter $d_1$, a tubular displacement body having an external diameter $d_2$ mounted coaxially within said reaction tube and extending along the entire length of said reaction tube, the ratio of diameter $d_2$ to diameter $d_1$ being greater than 0.8.

* * * * *